(12) United States Patent
Klapper

(10) Patent No.: US 10,746,800 B2
(45) Date of Patent: Aug. 18, 2020

(54) ACCUMULATOR OPERATED RELAY TEST DEVICE 1

(71) Applicant: OMICRON ELECTRONICS GMBH, Klaus (AT)

(72) Inventor: Ulrich Klapper, Rankweil (AT)

(73) Assignee: OMICRON ELECTRONICS GMBH, Klaus (AT)

(*) Notice: Subject to any disclaimer, the term of this patent is extended or adjusted under 35 U.S.C. 154(b) by 135 days.

(21) Appl. No.: 15/774,918

(22) PCT Filed: Oct. 21, 2016

(86) PCT No.: PCT/EP2016/075347
§ 371 (c)(1),
(2) Date: May 9, 2018

(87) PCT Pub. No.: WO2017/080789
PCT Pub. Date: May 18, 2017

(65) Prior Publication Data
US 2018/0328991 A1  Nov. 15, 2018

(30) Foreign Application Priority Data
Nov. 10, 2015 (AT) .............................. A 50956/2015

(51) Int. Cl.
*G01R 31/02* (2006.01)
*G01R 31/327* (2006.01)
(Continued)

(52) U.S. Cl.
CPC ..... *G01R 31/3278* (2013.01); *G01R 31/3648* (2013.01); *G01R 31/385* (2019.01);
(Continued)

(58) Field of Classification Search
CPC . A61B 5/055; A61B 5/0515; A61B 2090/374; A61B 2503/04; G01R 33/4828;
(Continued)

(56) References Cited

U.S. PATENT DOCUMENTS 3,924,178 A  12/1975  Lockyer et al.
4,628,268 A  12/1986  Matsubar
(Continued)

FOREIGN PATENT DOCUMENTS

CN  203643575  6/2014
JP  59-110320  6/1984
(Continued)

OTHER PUBLICATIONS

Korea Notif. of Refusal conducted in counterpart Korea Appl. No. 10=2018-7016434 (dated May 22, 2019) (w/ English translation).
(Continued)

*Primary Examiner* — Raul J Rios Russo
(74) *Attorney, Agent, or Firm* — Greenblum & Bernstein, P.L.C.

(57) ABSTRACT

A method and test device for testing protection relays, the test device having a signal generator. The signal generator supplies a signal as pulses having pause times, which alternate over time. Signal level is reduced during the pause times and at least one pulse has an amplitude at least higher than one of the preceding pulses. A supply voltage is supplied by an accumulator providing electric energy for generating the pulses. Via the accumulator, a greater mobility and flexibility is ensured, and fuel-fed power units or emergency power units may be omitted. In order to reduce the load (average energy) on the accumulator, the signal generator emits the signal as pulses having pause times. The pulse amplitudes may have an increasing trend to reach a
(Continued)

switching threshold. This allows the use of smaller and more compact, which is important for a portable test device.

24 Claims, 2 Drawing Sheets

(51) Int. Cl.
| | |
|---|---|
| G01R 31/385 | (2019.01) |
| G01R 33/48 | (2006.01) |
| G01R 33/54 | (2006.01) |
| G01R 33/50 | (2006.01) |
| G01R 33/56 | (2006.01) |
| G01R 31/36 | (2020.01) |
| H01H 71/12 | (2006.01) |
| A61B 5/055 | (2006.01) |
| A61B 5/05 | (2006.01) |
| A61B 90/00 | (2016.01) |

(52) U.S. Cl.
CPC ......... *G01R 33/4828* (2013.01); *G01R 33/50* (2013.01); *G01R 33/543* (2013.01); *G01R 33/5608* (2013.01); *H01H 71/121* (2013.01); *A61B 5/055* (2013.01); *A61B 5/0515* (2013.01); *A61B 2090/374* (2016.02); *A61B 2503/04* (2013.01)

(58) Field of Classification Search
CPC ... G01R 33/543; G01R 33/50; G01R 33/5608
USPC .................................................. 324/300, 318
See application file for complete search history.

(56) References Cited

U.S. PATENT DOCUMENTS

| 5,978,191 | A | 11/1999 | Bonniau et al. |
| 2003/0160619 | A1 | 8/2003 | Parker |
| 2003/0169545 | A1* | 9/2003 | Tallman ................. H02H 3/044 361/42 |
| 2005/0068038 | A1 | 3/2005 | Hsiao et al. |
| 2006/0076958 | A1 | 4/2006 | Tsau et al. |
| 2007/0257680 | A1 | 11/2007 | Klijn et al. |
| 2009/0251001 | A1* | 10/2009 | Kojima ................. H03F 1/0211 307/18 |
| 2010/0060336 | A1* | 3/2010 | Kojima ..................... H03F 1/30 327/243 |
| 2013/0140896 | A1* | 6/2013 | Tzinker ................. H02M 3/156 307/43 |
| 2013/0237280 | A1 | 9/2013 | Deak et al. |
| 2013/0245869 | A1* | 9/2013 | Nishida ................. B60L 3/0069 701/22 |
| 2017/0082691 | A1* | 3/2017 | Murahari ........... G01R 31/3272 |

FOREIGN PATENT DOCUMENTS

| JP | 2011-176919 | 9/2011 |
| RU | 2024888 | 12/1994 |
| RU | 2073269 | 11/1997 |
| RU | 2240622 | 11/2004 |
| SU | 393701 | 8/1973 |
| WO | 94/10578 | 5/1994 |

OTHER PUBLICATIONS

Russia Search Report conducted in counterpart Russia Appl. No. 2018121278/28A 50956/2015 (dated Mar. 4, 2019).
Austria Search Report conducted in counterpart Austria Appl. No. A 50956/2015 (dated Jul. 19, 2016).
Korea (Second) Notif. of Refusal conducted in counterpart Korea Appl. No. 10-2018-7016434 (dated Oct. 18, 2019) (w/ English translation).
China Office Action conducted in counterpart China Appln. No. 201680065605.6 (dated Nov. 13, 2019) (w/ English translation).

* cited by examiner

ACCUMULATOR OPERATED RELAY TEST DEVICE 1

The present invention refers to a method and a test device for testing a protection relay, wherein in the test device a signal is generated and the signal is supplied to the protection relay. A test arrangement of test devices is also described.

In the field of energy installations, in particular in electric energy transmission networks, protection relays are used for monitoring the installation (primary system). In order to better manipulate the real primary currents and voltages, the currents are converted by current converters and the voltages are converted by voltage converters into smaller, easier-to-be-manipulated secondary variables, which are processed in the protection relay. However, the protection relay is at any time aware of the state of the primary current and voltage levels. Protection relay may determine, based on various criteria, whether in the primary system a fault is present, and, depending on the fault, emit immediately or after a defined delay time, a switch-off command to one or more power switches, in order to terminate the faulty condition in the installation. Various protection relays operate together in such a way that faults are rapidly, securely, but also selectively deactivated. Selectively means that possibly only the portion of the energy transmission network, in which a fault has occurred, is deactivated, in order to allow an undisturbed continuation of operation in many other parts of the energy transmission network.

A function of a protection relay is the overcurrent time protection. In this case, if the nominal current is exceeded, depending on the value of the current, the switch-off command is issued, at different speeds. For safety reasons, it is necessary or required that safety devices of an electric energy transmission network, such as the protection relay, are tested at regular intervals in order to asses that they are operating properly.

The test of a protection relay with overcurrent time protection function may for example occur in that in the protection relay a test current, one-or three phase, is supplied and the reaction of the protection relay is observed. Test devices for testing protection relays are also called "relay test apparatus". Usually the protection relay is separated from the electric transmission network and directly connected to a test device, and secondary variables are fed through a current converter. However direct tests of primary variables are also possible. It is checked whether the protection relay does not trigger at currents below a current threshold, such as nominal currents, and how fast the protection relay triggers at different faulty conditions. In case of an overcurrent time protection, usually, the switch-off speed is faster in case of increasing current levels. The test device is provided with an input, which is connected to the power switch output of the protection relay and which is configured for recording the time of triggering of the protection relay, thus when it would switch the power switch. If one wants to determine the signal threshold, at which a protection relay reacts, a small current may be increased in a continuous way until the protection relay reacts. Such a test may last for more than a few seconds, or even minutes.

Since this test normally occurs in the field on site, and an electric socket is not always readily available, the test device is sometimes also powered by electric power units. This means that for the test a current generator has to be transported, but this increases the costs and the difficulty of manipulation (weight, size, fuel, etc.). In particular at sites which are difficult to reach, such as only by foot, which is not unusual in the case of electric energy transmission networks, this immobility represents a huge drawback.

The object of the present invention is thus to provide a test device, which is easier and more efficiently manipulated and which reduces the described drawbacks.

This object is achieved by a method and a device, which are characterized in that a signal as pulses with pause times is output by a signal generator provided with the test device, wherein the pulses of the signal and the pause times alternate over time, during the pause times the level of the signal is reduced and at least one pulse has an amplitude which is higher than one of the preceding pulses. The test device is supplied by an accumulator with a supply voltage, which thus provides electric energy for generating the pulses.

The object is also achieved by a test arrangement, in which a test device is connected to a protection relay, and has a signal output, through which a signal is supplied to a signal input of the protection relay, and has a reaction input, which is connected with the switching output of the protection relay.

The use of an accumulator allows a higher mobility and flexibility and the omission of fuel-supplied power units or emergency power units. In operation, the accumulator is subject to heavy loads within short times, in particular when ramps for determining signal thresholds have to be run, as said, and the test is relatively long. In order to keep the load on accumulators at a lower level, the signal generator provides the signal as pulses with pause times, wherein the amplitudes of pulses may increase monotonically with a general rising trend in order to reach the switching threshold. A rising trend means that between the pulses at higher amplitudes also other pulses, with a lower amplitude with respect to trend, may occur. Since the signal is generated in the form of individual pulses, the average energy required is reduced and the accumulator is stressed less. This allows, in spite of the voltages and (normally very high) currents required for the test and adapted to the electric transmission network, the use of smaller and more compact accumulators, which is important for example for a portable device.

The signal may for example represent a current or a voltage, while the method may also be applied for other signals.

The signal generator may comprise a voltage and/or a current source.

Furthermore, the test device may have a first number of signal outputs, which generate the first number of signals.

The test device may also have a second number of reaction inputs.

Advantageously, three current outputs and three voltage outputs can be provided on the test device in order to be able to reproduce the signals of a three-phase branch in the energy network. This allows a three-phase network to be simulated and a three-phase protection relay to be tested. However, the signals of the individual phases do not necessarily have to have the same amplitude. A phase shift of 120° between the phases is usual but may also deviate completely in the event of an error. Advantageously, two reaction inputs can also be present at the test device in order to be able to detect various reactions of the protection relay, such as, for example, a triggering or an excitation. An excitation may mean that a signal threshold has been exceeded briefly, but not long enough to produce a triggering.

The protection relay may switch within a reaction time, after the signal has reached a signal threshold, wherein the test device determines the level of the signal upon reaching the signal threshold.

It is to be noted that the respective pulse durations reach the reaction time of the protection relay, in order to allow the testing of the correct operation of the protection relay. The duration to be selected for the pause times depends on the energy of pulses, i.e. the amplitude and pulse duration. The reaction time of the protection relay in case of high signals to be switched is normally lower than in case of lower signals.

In particular the additional determination of reaction time t from reaching the signal threshold to switching of the reaction output is advantageous.

The amplitudes of the pulses of the signal may increase over time by a preferably fixed signal difference. This means that the signal can be approximated step by step to the signal threshold and, for example, an overcurrent time protection can be checked.

The pause times may be variable and depend on the amplitude of the pulses of the signal at a time.

This can be achieved, for example, by a pulse threshold at which the pause times are increased by a factor k. Thus, from the pulse threshold, a different slope of the envelope of the signal would result. It is also conceivable that the pause times are influenced, for example, by a plurality of pulse thresholds, or are variable in another way. Variable pause times allow the accumulator to have more time for "recovery" from larger currents. The signal difference could also be variable.

The signal can advantageously be lowered during the pause times to a value of less than 1% of the preceding pulse, preferably to zero. This minimizes the average power consumption from the accumulator.

The accumulator may advantageously have an energy density of at least 500 J/g. The accumulator or a part thereof may be based on lithium-ion or lithium polymer technology.

The test device may also be portable, wherein the reduced weight due to the use of an accumulator is particularly advantageous in the field.

An adaptation device may be supplied with the power voltage and the signal generator may be supplied with the intermediate voltage.

In this way, for example, it is possible to convert a high supply voltage of an accumulator into a lower intermediate voltage, while the current provided by the accumulator may be converted into a higher current, and thus powering the signal generator. This is advantageous, since the signal generator generally requires higher currents, but obviously also a low power supply voltage of accumulator may be converted into a high intermediate voltage and a high current into a low current.

The adaptation device should possibly work with high clock frequencies, so that additional lowpass filters for suppressing the generated disturbances are useful.

This adaptation device may comprise a step-up converter and/or a step-down converter.

Advantageously, at least a part of the adaptation device and/or of the signal generator may be deactivated if required by means of an emergency-off circuit.

Since the current generated by the adaptation device may be very high, it would be difficult to separate the same. Thus at least a part of the adaptation device, preferably the power electronics, is deactivated in a targeted mode, wherein a redundancy of the deactivated parts ensures the required safety. This redundancy may for example be obtained by the fact that adaptation device and signal generator are deactivated.

The form of the signal may be determined by a control unit, wherein the result of the control unit is processed by a digital-analog converter for generating the signal, and the digital-analog converter drives the signal generator.

The present invention is explained in the following with reference to FIGS. 1 to 6, which show, as an example, schematically and in a non-limiting way, advantageous embodiments of the invention. In particular:

Figure 1:
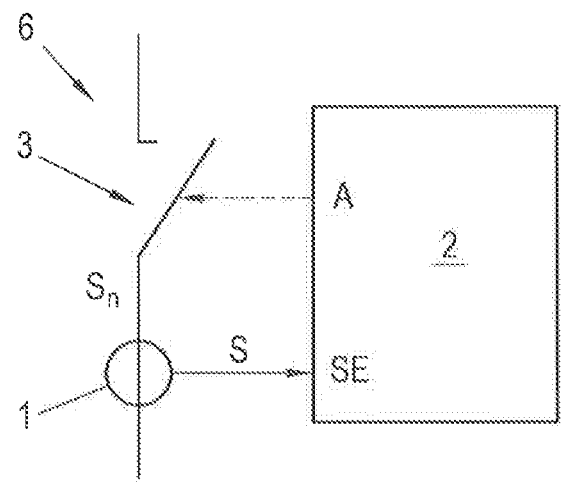
FIG. 1 shows a protection relay 2 in a power supply network 6
Figure 4:
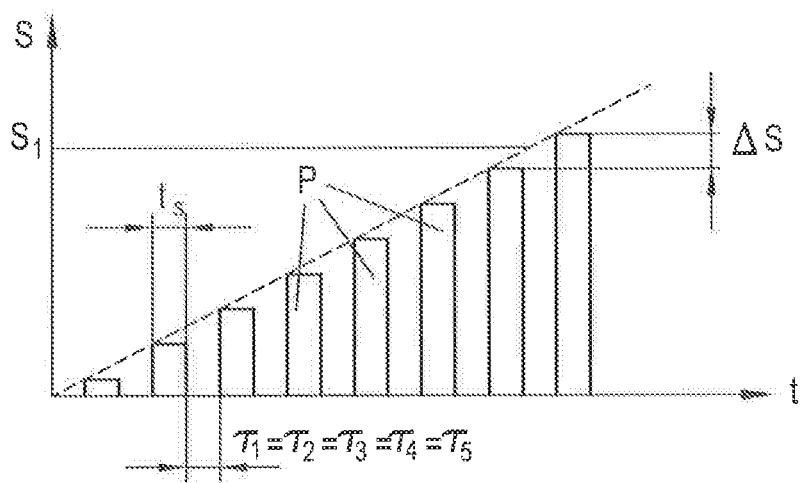
Figure 5:
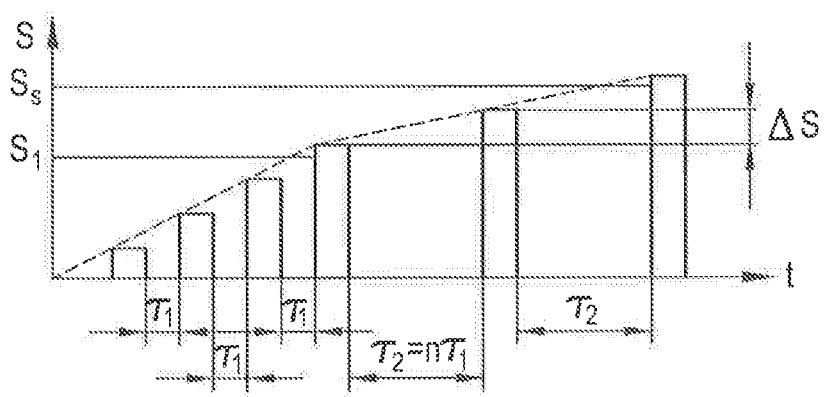
Figure 6:
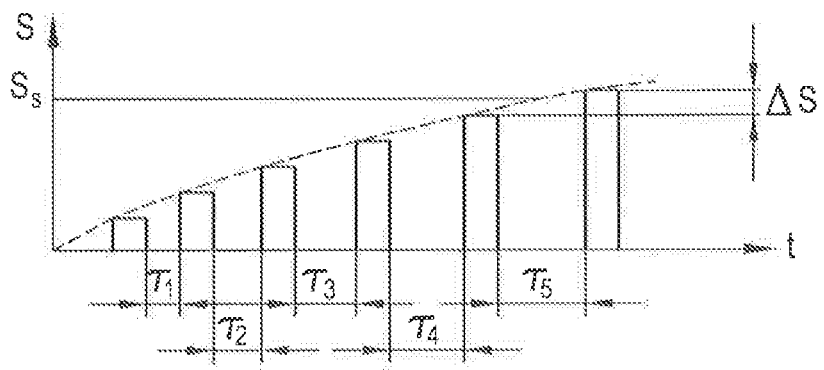

FIG. 4 shows the plot of a signal S having fixed pause times $\tau_1 = \tau_2 = \tau_3 = \tau_4 = \tau_5$ FIG. 5 shows the plot of a signal S having a pulse threshold $S_1$ FIG. 6 shows the plot of a signal S having strictly monotonic increasing pause times $\tau_1 < \tau_2 < \tau_3 < \tau_4 < \tau_5$ In FIG. 1 a protection relay 2 is connected via the signal input SE and the switching output A with the electrical power supply network 6. The electrical power supply network 6 can also be a line section or a line branch of a large power network. An optionally present signal converter 1 measures a presignal $S_n$ (primary variable)—when the signal is represented by a current, the signal converter 1 is usually designed as a current converter or current sensor—of the power supply network 6 and converts this into a signal S (secondary variable), which is supplied to the protection relay 2 via the signal input SE. For example, in low-voltage networks, it is also possible to supply the secondary signal $S_n$ directly to the protection relay. For example, in the case of a function as overcurrent time protection, the protection relay 2 is designed such that it switches the switching output A, and thus opens the associated circuit breaker 3 of the electrical power supply network 6 as soon as a specific preset signal threshold $S_s$ is exceeded for a fixed period of time. Thus, the electrical circuit of the power supply network 6 (or of the respective network segment) is interrupted, whereby, for example, protection against overcurrents is ensured in the electrical power supply network 6.

Figure 2:
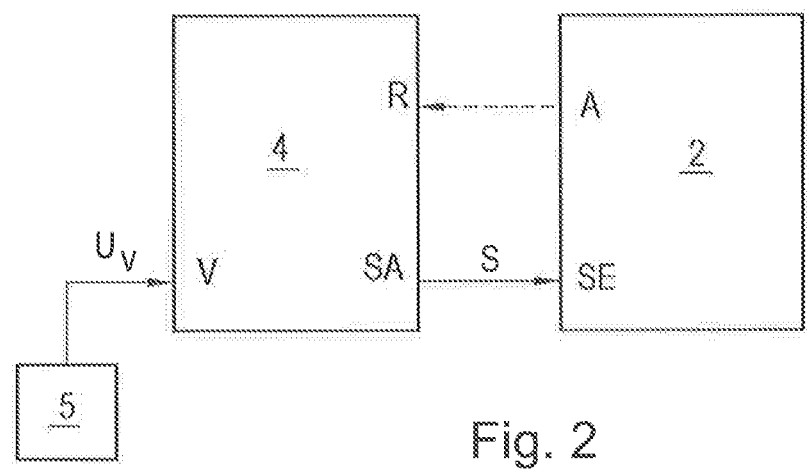
FIG. 2 shows a protection relay 2 which is connected to a test device 4.

In order to determine the signal threshold $S_s$ at which the protection relay 2 actually switches, the protection relay 2 is disconnected from the power supply network 6 and connected to a test device 4, as shown in FIG. 2. The test device 4 has a signal output SA and a reaction input R. For the functional test, the connection from the protection relay 2 to the signal converter 1 (or, if no current converter is present, the connection to the power supply network 6) and to the power switch 3 is interrupted and the signal output SA of the test device 4 is connected with the signal input SE of the protection relay 2, as well as the switching output A of the protection relay 2 is connected with the reaction input R of the test device 4. The test device 4 in turn is supplied by a accumulator 5, which is preferably integrated in the test device 4, via a supply input V with a supply voltage $U_v$. To test the protection relay 2, a signal S is sent from the test device 4 to the protection relay 2.

If, for example, the protection comprises an over-current time protection, the protection relay 2 switches within a reaction time $t_4$ after the signal S has reached the signal threshold $S_S$ to be determined. The test device 4 determines the level, i.e. the amplitude, of the signal S, at which the protection relay 2 reacts.

For this purpose, an evaluation unit 7 is provided in the test device 4, which is connected to the reaction input R and detects a switching pulse of the protection relay 2 which is output at the switching output A.

Figure 3:
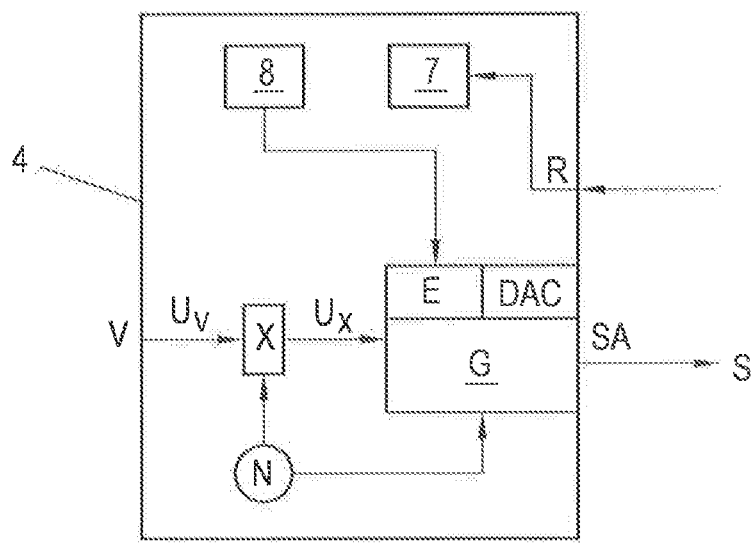
FIG. 3 shows a possible structure of a test device 4.

A signal generator G outputs the signal S as pulses P with pause times $\tau_1$, $\tau_2$, $\tau_3$, $\tau_4$, $\tau_5$, at the signal output SA, whereby the pulses P of the signal S and pause times $\tau_1$, $\tau_2$, $\tau_3$, $\tau_4$, $\tau_5$ alternate over time t (FIG. 3). During the pause times $\tau_1$, $\tau_2$, $\tau_3$, $\tau_4$, $\tau_5$, the amplitude of the signal S is lowered to a low value, for example 1% of the previous amplitude or even zero. At least one pulse P has a higher amplitude than at least one of the preceding pulses P in order to reproduce an ascending signal S, as shown in FIG. 4 in an exemplary manner. By implementing the pause times $\tau_1$, $\tau_2$, $\tau_3$, $\tau_4$, $\tau_5$, the accumulator 5 is less stressed.

An embodiment in which also the response time $t_A$ of the protection relay 2 is determined by the test device 4, preferably in the evaluation unit 7, is also particularly advantageous. The response time $t_A$ of the protection relay 2 thus describes the time from the signal S reaching the signal threshold $S_s$ until the switching of the reaction output R.

An adaptation device X located in the test device 4 can convert the supply voltage $U_V$ of the accumulator 5 into an intermediate voltage $U_x$, which in turn supplies the signal generator G, as also shown in FIG. 3.

The adaptation device X can convert high voltages into low voltages and low currents into high currents, or vice versa, too.

This adaptation device X may include a step-up converter and/or a step-down converter.

Moreover, at least part of the adaptation device X and/or of the signal generator G can be deactivated by means of an emergency-off circuit N, as required.

This part of the adaptation device X may, for example, comprise power electronics, which is part of a converter circuit. Since high currents are difficult to separate cleanly, it is possible to realize an emergency-off circuit N, with the targeted deactivation of (redundant) circuit parts, such as, for example, the power electronics.

The test device 4, or the signal generator G, may include a voltage source and/or a current source and generate a voltage or current signal S.

In addition, the form of the signal S can be calculated by a control unit E, wherein the result of the control unit E is processed by a digital/analog converter DAC for generating the signal S and the digital/analog converter DAC drives the signal generator G.

For this purpose, an input unit 8 may be provided in the test device 4, which is connected to the control unit E, through which for example a determined test to be executed may be set up. The control unit E and the digital/analog converter DAC can be located in the signal generator G.

Furthermore, the signal generator G can have n>1 signal outputs which generate n signals $S_n$ so that a protection relay 2 of a multi-phase network can be tested simultaneously for all n phases.

Advantageously, n=3, whereby a three-phase network can be simulated. Thus, a three-phase protection relay 2 can be tested. However, the n signals $S_n$ do not necessarily have to be the same.

Furthermore, the test device 4 can have a second number of reaction inputs R in order to detect different reactions of the protection relay 2, such as, for example, a triggering or an excitation.

A signal S is generated at a certain level (amplitude) over a pulse duration $t_s$ and lowered after the pulse duration $t_s$ for a pause time $\tau_1$, $\tau_2$, $\tau_3$, $\tau_4$, $\tau_5$. Pause times $\tau_1$, $\tau_2$, $\tau_3$, $\tau_4$, $\tau_5$ in the range of 500 ms to 1 s are the rule. The length of the pulse duration $t_s$ must be at least as great as the response time $t_A$ of the protection relay 2, since otherwise the correct function of the protection relay 2 can not be tested. At least a pulse duration $t_s$ of 10 ms is required in most cases, usual pulse durations $t_s$ are approximately 30 ms, but pulse durations in the second range are also possible. The decisive factor here is the reaction time $t_A$ of the protective relay 2, which in turn depends on the level of the signal to be switched. A higher current has normally to be switched faster, i.e. with a shorter reaction time $t_A$ than for a lower current.

The pulse duration $t_s$ is shown as a constant in FIGS. 4 to 6, but may also vary, for example, depending on the magnitude of the signal S. This can be used, for example, to keep the energy of a pulse P low by reducing the pulse durations $t_s$ with increasing amplitude. After the pause time $\tau_1$, $\tau_2$, $\tau_3$, $\tau_4$, $\tau_5$ has elapsed, the signal is supplied, increased by the signal difference $\Delta S$ for a further pulse duration $t_s$, whereupon again a pause time $\tau_1$, $\tau_2$, $\tau_3$, $\tau_4$, $\tau_5$ follows. This advantageously takes place until the protection relay 2 responds or triggers. Advantageously, the signal difference $\Delta S$ is always constant and positive. However, it is also conceivable that the signal difference $\Delta S$ is variable, or negative or zero in sections, which may depend, for example, on the current level of the signal S. In order to reach the signal threshold $S_s$, however, at least one pulse P must have a higher amplitude than at least one of the preceding pulses P, unless the amplitude of the first pulse P of the signal S reaches the signal threshold $S_s$. In this case, the protection relay 2 switches immediately.

The pause times $\tau_1$, $\tau_2$, $\tau_3$, $\tau_4$, $\tau_5$ of the signal S which continue between the individual pulses P of the signal S can always have the same length, but also depend on the current amplitude of the signal S or another factor.

Since the choice of the pause times $\tau_1$, $\tau_2$, $\tau_3$, $\tau_4$, $\tau_5$ preferably depends on the selected pulse duration $t_s$, it is therefore possible to react both to variable pulse durations $t_s$, and the average energy of the pulses P may be lowered in sections, for example. A lower energy consumption of the test device 4 and thus a lower energy absorption from the accumulator 5 will result in a lower load on the accumulator 5.

FIG. 4 shows an exemplary plot of a signal S over time t. The dashed envelope of the pulses of signal S interrupted by pause times $\tau_1$, $\tau_2$, $\tau_3$, $\tau_4$, $\tau_5$ indicates the rising signal S, wherein in this example the pause times $\tau_1$, $\tau_2$, $\tau_3$, $\tau_4$, $\tau_5$ are constant and the level of successive pulses P of the signal S at a constant signal difference $\Delta S$ increases linearly.

A plot according to FIG. 5 is also possible, in which the pause times $\tau_1$, $\tau_2$, are increased as soon as the amplitude of the current pulse P of the signal S reaches a pulse threshold $S_1$. With a constant signal difference $\Delta S$, this results in the envelope shown with a dashed line in the form of a rising signal S, wherein the slope of the signal S is being reduced after reaching a pulse threshold $S_1$. The advantage of increasing the pause times with increasing amplitude lies in the fact that the average accumulator load must not increase with amplitude, since the longer pauses can compensate for the increasing power requirements for the pulses.

In the pause times $\tau_1$, $\tau_2$, $\tau_3$, $\tau_4$, $\tau_5$ the level of the signal S is reduced. Advantageously, the signal S in the pause times $\tau_1$, $\tau_2$, $\tau_3$, $\tau_4$, $\tau_5$, may be set to a value of less than 1% of the previous pulse P, or even to zero, as shown in FIGS. 4-6, which can extend the life of the accumulator 5.

Advantageously, the accumulator 5 can have an energy density of at least 500 J/g.

Advantageously, the pause times $\tau_1$, $\tau_2$, $\tau_3$, $\tau_4$, $\tau_5$ increase continuously as the signal S increases. The pause times $\tau_1$, $\tau_2$, $\tau_3$, $\tau_4$, $\tau_5$ can thus be strictly monotonically increasing from pulse P to pulse P, resulting in a dashed envelope for the signal S with a slope reduced over time t. This embodiment is also shown in FIG. 6 with a constant signal difference ΔS.

Of course, it is also conceivable that the pause times $\tau_1$, $\tau_2$, $\tau_3$, $\tau_4$, $\tau_5$ are reduced (for example, in sections), or remain constant in sections.

Of course, mixed variants of the just mentioned profiles, as well as further variations of the pause times $\tau_1$, $\tau_2$, $\tau_3$, $\tau_4$, $\tau_5$ as well as of the signal difference ΔS are possible depending on the current amplitude of the pulse P. Thus, for example, a plurality of pulse thresholds $S_1$ may be present and the signal difference ΔS and/or the pause times $\tau_1$, $\tau_2$, $\tau_3$, $\tau_4$, $\tau_5$ may be changed several times.

The test device 4 can be have a portable configuration, due to the low weight, by using an accumulator 5, which is particularly advantageous for a use in the field.

The invention claimed is:

1. A method for testing a protection relay comprising:
   generating a signal in a test device, and
   supplying the signal to the protection relay,
   wherein the test device includes a signal generator configured to output the signal as pulses having pause times,
   wherein the pulses of the signal and the pause times alternate over time, the level of the signal is reduced during the pause times and at least one pulse has an amplitude which is higher than at least one of a preceding pulse, and
   supplying a supply voltage from an accumulator to the test device as electric energy for generating the pulses.

2. The method of claim 1, wherein the signal represents a voltage or a current.

3. The method of claim 1, wherein the protection relay switches within a reaction time after the signal has reached a signal threshold, and the method further comprising determining in the test device a level of the signal upon reaching the signal threshold.

4. The method of claim 3, further comprising determining the reaction time.

5. The method of claim 1, wherein amplitudes of the pulses of the signal increase over time.

6. The method of claim 1, wherein the pause times depend on an amplitude of at least one pulse of the signal.

7. The method of claim 1, wherein the signal during the pause times is smaller than 1% of a preceding pulse.

8. The method of claim 1, wherein an adaptation device is supplied with the supply voltage, and the method further comprises supplying the signal generator with an intermediate voltage by the adaptation device.

9. The method of claim 8, further comprising deactivating at least a part of the adaptation device by an emergency-off circuit.

10. The method of claim 1, wherein a form of the signal is determined by a control unit and a result of the control unit is processed by a digital/analog converter in order to generate the signal (S) and the digital/analog converter drives the signal generator.

11. The method of claim 5, wherein the amplitudes of the pulses increase over time by a fixed signal difference.

12. The method of claim 7, wherein the signal during the pause times is zero.

13. The method of claim 1, further comprising deactivating at least a part of the signal generator by an emergency-off circuit.

14. A test device for testing a protection relay comprising:
    a signal output configured to output a signal;
    a signal generator configured for outputting the signal in a form of pulses having pause times, wherein the pulses of the signal and the pause times alternate over time, a level of the signal is reduced during the pause times and at least one pulse has an amplitude which is at least higher than one of a preceding pulse; and
    an accumulator, which provides a power voltage for the test device.

15. The test device of claim 14, wherein the test device comprises an adaptation device configured to convert the power voltage into an intermediate voltage to be supplied to the signal generator.

16. The test device of claim 15, wherein the adaptation device comprises at least one of a step-up converter or a step-down converter.

17. The test device of claim 14, wherein the signal generator comprises at least one of a voltage source or a current source.

18. The test device of claim 14, wherein the signal output comprises a plurality of signal outputs that are configured to output a plurality of signals.

19. The test device of claim 14, further comprising an emergency-off circuit configured to deactivate at least a part of the signal generator.

20. The test device of claim 14, wherein the accumulator has an energy density of at least 500 J/g.

21. The test device of claim 14, wherein the test device is configured as a portable test device.

22. The test device of claim 14, further comprising a control unit configured to determine a form of the signal and a digital/analog converter configured to process a result of the control unit in order to generate the signal.

23. A test arrangement comprising the test device of claim 14, wherein the test device is connectable to a protection relay, having a signal input and a switching output, so that the signal output from the signal output of the test device is supplyable to the signal input of the protection relay, and a reaction input of the test device is connectable to the switching output of the protection relay.

24. The test device of claim 15, further comprising an emergency-off circuit configured to deactivate at least a part of the adaptation device.

* * * * *